(12) United States Patent
Fuertes et al.

(10) Patent No.: US 7,612,198 B2
(45) Date of Patent: *Nov. 3, 2009

(54) SOLUBLE HIGHLY BRANCHED GLUCOSE POLYMERS

(75) Inventors: Patrick Fuertes, Lomme (FR); Jean-Michel Roturier, La Chapelle d'Armentieres (FR); Carole Petitjean, Marquette lez Lille (FR)

(73) Assignee: Roquette Freres, Lestrem (FR)

( * ) Notice: Subject to any disclaimer, the term of this patent is extended or adjusted under 35 U.S.C. 154(b) by 566 days.

This patent is subject to a terminal disclaimer.

(21) Appl. No.: 11/015,640

(22) Filed: Dec. 20, 2004

(65) Prior Publication Data

US 2005/0159329 A1 Jul. 21, 2005

(30) Foreign Application Priority Data

Dec. 19, 2003 (FR) .................... 03 15085

(51) Int. Cl.
*C08B 30/00* (2006.01)
*C08B 30/18* (2006.01)
*C08B 30/20* (2006.01)

(52) U.S. Cl. .................... 536/102; 536/103; 536/123.1; 536/124; 536/4.1; 514/778; 426/658

(58) Field of Classification Search .................. 536/102, 536/103, 123.1, 124, 4.1; 514/778; 426/658
See application file for complete search history.

(56) References Cited

U.S. PATENT DOCUMENTS 6,861,519 B2 * 3/2005 Backer et al. ............... 536/102
2003/0134394 A1 7/2003 Antrim et al.

FOREIGN PATENT DOCUMENTS

| EP | 0 574 721 | 12/1993 |
| EP | 1 369 432 | 12/2003 |
| FR | 2 499 588 | 8/1982 |
| WO | WO 00/18893 | 4/2000 |
| WO | WO 00/66633 | 11/2000 |
| WO | WO 02/10427 | 2/2002 |
| WO | WO 03/018639 | 3/2003 |

* cited by examiner

*Primary Examiner*—Shaojia Anna Jiang
*Assistant Examiner*—Michael C Henry
(74) *Attorney, Agent, or Firm*—Young & Thompson

(57) ABSTRACT

The invention relates to soluble highly branched glucose polymers, having a reducing sugar content of less than 1%, a level of α-1,6 glucoside bonds of between 13 and 17% and an Mw having a value of between $0.9 \times 10^5$ and $1.5 \times 10^5$ daltons, characterized in that their branched chain length distribution profile consists of 70 to 85% of DP of less than 15, of 10 to 16% of DP of between 15 and 25 and of 8 to 13% of DP greater than 25.

21 Claims, No Drawings

SOLUBLE HIGHLY BRANCHED GLUCOSE POLYMERS

The subject of the invention is soluble highly branched glucose polymers having a low reducing sugar content, a remarkably high level of α-1,6 glucoside bonds, a narrow range of high molecular weights, and a very particular branched chain length distribution profile.

The invention also relates to soluble highly branched glucose polymers having a low intrinsic viscosity.

The invention makes these soluble highly branched glucose polymers more particularly destined for food, and especially medical, applications.

The expression "branched chain length distribution profile" is understood to mean, for the purposes of the invention, the size distribution, expressed as degree of polymerization (or DP), of the linear α-1,4 glucoside chains linked to other linear α-1,4 glucoside chains by α-1,6 branching points.

The invention also relates to a method for manufacturing the said soluble highly branched glucose polymers.

The glucose polymers which are industrially accessible are conventionally prepared by hydrolysis of natural or hybrid starches and of their derivatives.

Standard starch hydrolysates are thus produced by acid or enzymatic hydrolysis of starch from cereals or tubers. They are in fact a mixture of glucose and glucose polymers of extremely varied molecular weights.

These starch hydrolysates (dextrins, maltodextrins and the like) which are produced in industry (with a certain mean DP) consist of a wide distribution of saccharides containing both linear and branched structures.

Starch hydrolysates, and in particular maltodextrins, are more particularly used as transporters or fillers, texturing agents, spray-drying supports, film-forming agents, freezing regulators or anticrystallizing agents.

They can also be used as fat substitutes or for their nutritional supply.

At the intestinal level, starch hydrolysates are thus digested by pancreatic α-amylase which acts directly on the linear chains linked in α-1,4.

This targeted enzymatic digestion leads to the size of the said starch hydrolysates being reduced to limit dextrins, and then a number of enzymes linked to the intestinal mucous membrane (maltase, sucrase and α-dextrinase) carry on the hydrolysis of the linear saccharides and the residual branched saccharides to glucose units.

The kinetics of these various enzymatic digestions is then directly dependent on the structure of the starch hydrolysates.

For example, pancreatic α-amylase will act more easily on starch hydrolysates which are rich in linear oligosaccharides or have long chain branched structures, whereas it will act with greater difficulty or not at all on compact branched structures which have predominantly short chains.

In the state of the art, these two types of structure are generally used differently, according to the intended fields of application.

The first type of structures derived from starch (in particular that of oligosaccharides with a short DP) is used as source of glucose which can be directly assimilated by the body, in particular in three fields of application.

The first field of application is that of high-energy substrates for sports people.

Indeed, in the sports field, a drink which is consumed during physical activity which requires a lot of effort should instantly provide both the energy and the water necessary to compensate for the loss of fluid through perspiration.

The result is that a composition which is balanced in relation to carbohydrates is essential in order to obtain such a result.

A solution which is conventionally proposed for the optimum drink is to prepare short linear oligosaccharides with a DP of 3 to 6 having more compact branched glucoside structures, since these short oligosaccharides are absorbed at the highest rate, while retaining the osmolality at a moderate level, thus preventing the loss of fluids and side effects such as diarrhoea and cramps.

The second field of application is that of parenteral feeding, where nutritive solutions supplied by the venous route are designed to keep a patient in good health and to provide them with nutrients when they cannot be fed via their normal digestive system.

The choice is made here also to administer linear oligosaccharides with a DP of between 2 and 5 because these saccharides are hydrolysed by maltases in the kidney, thus releasing glucose that is then reabsorbed. Accordingly, the use of short linear oligosaccharides makes it possible to provide sufficient energy in an isotonic solution, without overhydrating the patient.

The third field of application is that of enteral nutrition, where it is necessary to provide drinks which may be either ingested orally or administered by the tubular route into the stomach or the small intestine.

For these enteral fluids, the major problem is however diarrhoea, due to an excessively high osmolality.

The second type of structures derived from starch, i.e. starch hydrolysate derivatives or starch derivatives having compact branched structures with short chains, is used to slow the release of assimilable glucose and/or provide a degree of osmolality, in particular in three fields of application.

The first field of application is that of the field of continuous and ambulatory peritoneal dialysis.

Patent EP 207,676 teaches that for use in dialysis, starch hydrolysates containing branched structures forming clear and colourless solutions at 10% in water, having a molecular weight (Mw) of $5 \times 10^3$ to $10^6$ daltons and a low polydispersity value or Vp, are preferred to linear oligosaccharides with a short DP.

This results in compositions which predominantly contain glucose polymers of high molecular weight of between $5 \times 10^3$ and $5 \times 10^5$ daltons, which do not contain or which contain very little glucose or oligosaccharides with a DP of less than or equal to 3, and no or very little glucose polymers with an Mw greater than $10^6$ daltons.

It can indeed be easily understood for this application in peritoneal dialysis that oligosaccharides with a short DP and of low molecular weight rapidly cross the peritoneal wall and are thus of no lasting benefit for the creation of an osmotic pressure gradient, and that polymers of very high molecular weight, which have no osmotic power, should be avoided and should even be prohibited since they are potentially dangerous if they happen to precipitate after their retrogradation.

In its patent EP 667,356, the Applicant Company proposed a method for manufacturing, from waxy starch, a starch hydrolysate which is completely soluble in water and which has a low polydispersity value of less than 2.8, and an Mw of between $5 \times 10^3$ and $1 \times 10^6$ daltons.

This method consists in hydrolysing, by an acid route, a starch milk consisting exclusively of amylopectin, and then in supplementing this acid hydrolysis with an enzymatic hydrolysis using a bacterial α-amylase, and chromatographing the hydrolysate obtained on macroporous strong cationic resins in alkali or alkaline-earth metal form.

It should be noted that at the time, the Applicant Company recommended using only starches almost exclusively composed of amylopectin and commonly called waxy starches as raw material in the said method, the starches containing a nonnegligible proportion of amylose not being suitable.

The second field of application is that of regulating the digestion or diet of diabetics.

It has indeed been proposed in U.S. Pat. No. 4,840,807 or in Patent Application JP 2001/11101 (registration No. 11/187,708), to extract only the regions with dense α-1,6 bonds as source of slowly absorbed carbohydrates, since the α-1,6 bonds are more difficult to degrade than the α-1,4 bonds.

Two families of products have thus been developed. The first involves the limit dextrins prepared by degradation of the regions with α-1,4 bonds with an α-amylase alone, and the second family relates to the dextrins prepared by degradation of the regions with α-1,4 bonds by the simultaneous action of an α-amylase and a β-amylase.

These limit dextrins obtained are then particularly resistant to human digestive enzymes.

However, these compounds have the disadvantage of having a very low molecular weight (between 10 000 and 55 000 daltons), which limits the use thereof in other fields of application.

The third field of application is that of blood plasma substitutes.

International Patent Application WO 03/18639 indeed recommends developing, solely from amylopectin, hyperbranched compounds in order to use them in surgical or therapeutic treatment of mammals or in diagnostic methods.

According to the teaching of this patent application, and more particularly in the field of blood plasma substitutes, these hyperbranched amylopectins are presented as being required to make it possible to resolve the major disadvantage of the first blood plasma substitutes produced—these are hydroxyethyl-starches or HES—i.e. their imperfect metabolism in the body.

In this patent application, the relative stability of the said hyperbranched amylopectins is mentioned in relation to their high content of α-1,6 bonds.

This high content of α-1,6 bonds is thought to then make it possible to sufficiently considerably reduce the degradation of amylopectin with α-amylase and to produce a polysaccharide which is degradable but which still possesses the properties of an ideal blood plasma substitute, namely its pharmacokinetic properties and its volume effect.

Moreover, the possibility of varying the distribution of the branching points is also envisaged in this Patent Application WO 03/018639 for controlling the kinetics of degradation of hyperbranched amylopectin in the desired direction.

However, the preparation of these hyperbranched amylopectins still has a major disadvantage.

Indeed, because of an excessively high branching (up to 25% of α-1,6 bonds) or an excessively short distance between the branching points, the effect obtained is diametrically opposed to that desired because the attack by α-amylase on these hyperbranched amylopectins can be considerably slowed or can no longer at all occur.

Steric hindrance is, in the regions of the molecule where the density of the branching points is high, such that access to α-amylase is no longer possible.

Under these conditions, the absence of enzymatic digestibility of these hyperbranched amylopectins does not particularly favour the use of such structures as blood plasma substitutes (accumulation of nondegraded products).

From the preceding text, it is evident that an unsatisfied need therefore exists to have highly branched glucose polymers which exhibit remarkable structural properties in terms of branched chain length distribution and intrinsic viscosity and which thereby confer on the products containing them higher capacities of shelf life and controlled digestibility.

These properties would then allow the use of these highly branched glucose polymers in fields of application as varied as the supply of high-energy substrates during physical activities and in the fields of peritoneal dialysis, enteral or parenteral nutrition, blood plasma substitutes, digestion regulation and the diet of diabetics.

The Applicant Company has had the merit of reconciling all these objectives which were up until now reputed difficult to reconcile, by devising and producing, at the cost of numerous research studies, novel soluble highly branched glucose polymers which are quite particular as regards their branched chain length distribution and their intrinsic viscosity.

The soluble highly branched glucose polymers in accordance with the invention are glucose polymers having a reducing sugar content of less than 1%, a level of α-1,6 glucoside bonds of between 13 and 17% and an Mw having a value of between $0.9 \times 10^5$ and $1.5 \times 10^5$ daltons, characterized in that their branched chain length distribution profile consists of 70 to 85% of DP of less than 15, of 10 to 16% of DP of between 15 and 25 and of 8 to 13% of DP greater than 25.

Preferably, the soluble highly branched glucose polymers in accordance with the invention have an intrinsic coefficient of viscosity "a" according to the MARK, HOUWINK and SAKURADA equation of less than or equal to 0.1.

The Applicant Company has already described in its Patent Application EP 1,369,432 soluble highly branched glucose polymers having a reducing sugar content of less than 1%, a level of α-1,6 bonds of between 12 and 30% and an Mw having a value of between 0.35 to $2 \times 10^5$ daltons.

However, none of the glucose polymers described and exemplified in the said patent application has the branched chain length distribution profile and the intrinsic viscosity of the highly branched glucose polymers in accordance with the invention, as will be exemplified below.

The determination of the reducing power, of the level of α-1,6 glucoside bonds and of the molecular masses of the soluble highly branched glucose polymers in accordance with the invention are carried out under the same conditions as those described in Patent Application EP 1,369,432.

The soluble highly branched glucose polymers in accordance with the invention then have a reducing sugar content of less than 1%, a level of α-1,6 glucoside bonds of between 13 and 17% and an Mw having a value of between $0.9 \times 10^5$ and $1.5 \times 10^5$ daltons.

Compared with the soluble highly branched glucose polymers of Patent Application EP 1,369,432 by the Applicant Company, the novel glucose polymers in accordance with the invention have narrower spectra of levels of α-1,6 glucoside bonds and of molecular weight.

However, the soluble highly branched glucose polymers in accordance with the invention are especially characterized by their chain length distribution profile.

The determination of the length of the branched chains of the soluble highly branched glucose polymers in accordance with the invention is carried out in two stages.

A first stage consists in debranching the said products (specific hydrolysis of the α-1,6 bond) with the aid of a bacterial isoamylase, followed by a second stage of identifying the degree of polymerization of the oligosaccharides released by steric exclusion chromatography (HPSEC) in comparison with pullulans of known size.

This technique consists in weighing 50 mg of products to be analysed and adding thereto 3.75 ml of water. After stirring this mixture, 0.5 ml of DiMethyl SulfOxide (DMSO) is added and the mixture heated at boiling temperature, with stirring, for 30 minutes. The temperature is then reduced to 45° C. and 0.25 ml of 1M sodium acetate buffer solution (brought beforehand to pH 3.5 with acetic acid) is added.

10 µl of an isoamylase extracted from *Pseudomonas amyloderasoma*, marketed by the company HAYASHIBARA, are then added (in an amount of 59 000 U/mg) and allowed to act at 45° C. for 1 hour. This enzymatic treatment is carried out twice in succession, and then the reaction is stopped by boiling for 3 minutes.

After adding 0.5 ml of n-butanol, stirring and storing at room temperature without stirring for 1 hour, the reaction medium is then centrifuged at 2600 rpm for 20 minutes, and the supernatant is demineralized with the aid of Amberlite 200 and Amberlite IRA-67 resins marketed by the companies FLUKA and SIGMA, respectively.

A final stirring and filtration on a nylon filter of porosity 0.45 µm are carried out before injecting onto the HPSEC column.

The parameters for HPSEC chromatography are as follows (on PWXL oligo column marketed by TSK and on SB 802+ 803+804+805 columns marketed by SHODEX):

Injection volume: 200 µl
Flow rate: 0.5 ml/min
Column temperature: 40° C.
Eluent: 0.2 M sodium nitrate+0.02% Na azide
Duration of elution: 180 min The size of the oligosaccharides released is determined by their elution time relative to the elution time for pullulans of known size.

The highly branched glucose polymers in accordance with the invention then have a branched chain length distribution profile consisting:

of 70 to 85% with a DP of less than 15,
of 10 to 16% with a DP of between 15 and 25,
of 8 to 13% with a DP greater than 25.

This branched chain length distribution profile leads to structures that are remarkable in regard to their high content of short branched chains (70 to 85% with a DP of less than 15) and its still relatively high content of medium size to long branched chains (15 to 30% with a DP greater than 15).

As a result, the soluble highly branched glucose polymers in accordance with the invention are rich in chains with predominantly short DP (more than 70% with a DP of less than 15), which makes it possible to obtain a compact branched structure containing predominantly short chains, and still contain, nevertheless, enough medium size to long chains (up to 30%), which the pancreatic α-amylases can easily digest in order to release glucose which can be assimilated by the body.

The soluble highly branched glucose polymers in accordance with the invention are also characterized by the value of their coefficient of intrinsic viscosity "a" according to the MARK, HOUWINK and SAKURADA equation.

The measurement of the coefficient of intrinsic viscosity "a" according to the MARK, HOUWINK and SAKURADA equation is used by the Applicant Company to illustrate the degree of compactness of the soluble highly branched glucose polymers in accordance with the invention.

It is known to a person skilled in the art that the MARK, HOUWINK and SAKURADA empirical formula which relates the intrinsic viscosity (η) of a polymer to its viscosimetric mean molecular mass (or $M_v$) is given by the following equation:

$$\eta = K \times (M_v)^a$$

where "K" and "a" are constants which depend on the nature of the polymer studied, on the nature of the solvent and on the temperature.

Under the analytical conditions according to the invention, the solvent used by the Applicant Company is a 0.2 M aqueous nitrate solution.

The constant "a" is related more particularly to the mean hydrodynamic volume occupied by the polymer in the solvent considered.

It is established in the state of the art that for a polymer in solution, the more the molecule is folded upon itself, the lower the value of "a". Conversely, for a "considerably open" molecule, the higher the value of "a".

The measurement of the coefficient "a" according to the MARK, HOUWINK and SAKURADA formula is determined by calculation, with the aid of the following equation:

$$\text{Log } \eta = \text{Log } K + a \text{ Log}(M_v)$$

The curve Log η is plotted as a function of Log ($M_v$) whose y-axis at the origin provides Log K and the slope of the line is the coefficient "a".

The viscosity and viscosimetric mean molecular mass values for the soluble highly branched glucose polymers in accordance with the invention are determined on a VISCOTEX capillary viscometer (model 250) coupled to an R410 refractometer, after separation on SHODEX SB 802+803+ 805 columns.

The chromatographic operating conditions are the following:

Injection: 100 µl
Flow rate: 0.5 ml/min
Column temperature: 35° C.
Eluent: 0.2 M sodium nitrate and 0.02% sodium azide
Analytical time: 180 min The operating conditions for the refractometric detection are:

Sensitivity R410: 16×
Temperature of the viscometer: 35° C.

The flow rate marker is a glycerine solution at 5% in the eluent.

The calibration of the detector is carried out with the aid of a PolyEthylene Oxide marketed by the company VISCOTEX, of known molecular weight, concentration and intrinsic viscosity.

The retreatment of this reference makes it possible to calculate the "mass constant" and the "viscosity constant" of the viscometer.

The retreatment of the elution peak for the flow rate marker makes it possible to calculate the reference time and the interdetector volumes.

The soluble highly branched glucose polymers in accordance with the invention then have a coefficient "a" calculated according to the MARK, HOUWINK and SAKURADA formula of less than 0.1, which indicates a state of high compactness, much higher than amylopectin (the standard amylopectin, under the same measurement conditions, indeed has a coefficient "a" value of 0.33).

The highly branched glucose polymers thus obtained are therefore particularly well suited to their use in fields of application where it is necessary to have compact and dense structures, for example in peritoneal dialysis or in the diet for diabetics.

The determination of the resistance of the soluble highly branched glucose polymers in accordance with the invention to the enzymes involved in the digestion of dietary carbohydrates is also an essential criterion in the choice of a food ingredient entering into the composition of formulations for use by sports people or intended for example for enteral and parenteral nutrition.

The Applicant Company had estimated the percentage or release of glucose by enzymatic digestion of the soluble highly branched glucose polymers described in its Patent Application EP 1,369,432 at a value of between 50 and 70%.

This resistance to hydrolysis is considerably higher than conventional maltodextrins and comparable to glycogen.

As will be exemplified below, the soluble highly branched glucose polymers in accordance with the invention ultimately release glucose in proportions similar to those described in the said patent EP 1,369,432, which still makes them suitable for use by sports people or for enteral and parenteral nutrition, but this release of glucose takes place much more slowly over time, which makes them advantageously destined for fields of application requiring the regulation of glycaemia such as the diet for diabetics.

No soluble highly branched glucose polymers exist, to the knowledge of the Applicant Company, which possess such a distribution of their branched chain lengths which makes it possible to use them in all the fields of application targeted by the present invention.

Advantageously, the highly branched glucose polymers in accordance with the invention may be classed into three subfamilies.

These three subfamilies have a branched chain length distribution profile which differs over their content of medium chains with a DP of between 15 and 25.

The first subfamily covers highly branched polymers which have at least 14% to at most 16% with a DP of between 15 and 25.

The second subfamily covers highly branched polymers which have at least 12% to at most 14% with a DP of between 15 and 25.

The third subfamily covers highly branched polymers which have at least 10% and at most 12% with a DP of between 15 and 25.

This variability in the distribution of the medium size chains allows the advantageous use of these subfamilies in food or medical applications where it is necessary to vary the digestibility of the soluble highly branched glucose polymers used.

These three subfamilies indeed all have a branched structure consisting of chains which are predominantly short in size, but in which the variable proportions of medium chains make it possible to modulate not only the degree of compactness thereof, but also to control the release of glucose, as will be exemplified below.

To prepare the soluble branched glucose polymers in accordance with the invention, the following steps are carried out successively which consist in:
1) preparing an aqueous starch solution having an amylose content of at least 30% by weight, preferably between 35 and 80% by weight,
2) treating the said solution with a branching enzyme and then a β-amylase successively,
3) carrying out a fractionation so as to recover the high molecular weight fractions,
4) collecting the highly branched glucose polymers thus obtained.

The preparation of the highly branched glucose polymers in accordance with the invention is carried out by modifying the operating conditions already described in Patent Application EP 1,269,432 by the Applicant Company.

First of all, unlike what was described in Patent Application EP 1,269,432, the choice of a particular starch quality is of great importance.

The Applicant Company indeed found that only starches whose amylose content exceeds 30% can serve as raw material in the method of the invention.

Maltodextrins, standard starches (which do not contain more than 30% of amylose) or waxy-type starches, regardless of their botanical origin, are absolutely not suitable for the manufacture of soluble highly branched glucose polymers in accordance with the invention.

It is moreover to the credit of the Applicant Company to have overcome a technical bias according to which in order to obtain a branched structure which is stable, compact and has a controlled digestibility, it is necessary to start with starches rich in amylopectin (as Patent Application WO 03/018639 teaches).

As will be exemplified below, the Applicant Company has found that on the contrary, it is through the choice of starches rich in amylose which are used as starting substrates that it is possible to obtain soluble highly branched glucose polymers in accordance with the invention.

It is also through the choice of the amylose content of the starches used as starting substrates that it is possible to obtain the three subfamilies defined above.

The second step of the method in accordance with the invention consists in treating the said starch solution with a branching enzyme.

In Patent Application EP 1,369,432, the Applicant Company recommended using 50 000 to 500 000 U of purified branching enzyme per 100 g on a dry basis of starch or starch derivative, at a temperature of between 25 and 95° C., preferably at a temperature of between 70 and 95° C., for a period of 18 to 24 hours.

The expression branching enzymes is understood to mean the branching enzymes chosen from the group consisting of glycogen branching enzymes, starch branching enzymes and any mixtures of these enzymes.

For the production of novel highly branched glucose polymers in accordance with the invention, the Applicant Company recommends preferably treating the solution of starch rich in amylose with 40 000 to 150 000 U of branching enzyme per 100 g of starch, at a temperature of between 25 to 80° C. for a period of 7 to 24 hours, preferably between 18 and 24 hours.

The third step of the method in accordance with the invention consists in causing a β-amylase to act on the starch solution thus treated.

The conditions for action (temperature and pH) of this enzyme are to cause the action of 0.05 to 0.5 ml of β-amylase of the SPEZYME BBA type from GENENCOR (at 1500 DP°/ml) per 100 g of starch at a temperature of 60° C., a pH of 4.9 to 5, for 1 to 3 hours, preferably for 2 hours.

A DP° unit means "Degrees of Diastatic Power", i.e. the quantity of enzyme contained in 0.1 ml of a solution containing 5% of the enzyme preparation which would produce a quantity of reducing sugars sufficient to reduce 5 ml of Fehling's solution when the sample is incubated with 100 ml of substrate for 1 hour at 20° C.

Contrary to what is described in Patent Application EP 1,369,432, use is therefore not made of any enzyme chosen from the group consisting of α-amylase, β-amylase, amyloglucosidase and α-transglucosidase, but indeed to preferably use β-amylase.

The Applicant Company has indeed found that it was through the choice of this particular enzyme that it is possible to easily obtain soluble highly branched glucose polymers in accordance with the invention.

At the end of this additional treatment, the soluble highly branched glucose polymers are obtained as a mixture with their products of enzymatic degradation, predominantly consisting of glucose and maltose.

The fourth step of the method consists in carrying out a fractionation with the aid of a technique chosen from the group comprising membrane separations and chromatographies, so as to recover high molecular weight fractions and low molecular weight fractions, as described in Patent Application EP 1,369,432 by the Applicant Company.

Regardless of the method used, the profiles obtained allow the separation of the high molecular weight polysaccharide fraction corresponding to the soluble highly branched glucose polymers in accordance with the invention, from the low molecular weight oligosaccharide fractions mainly consisting of glucose and maltose.

The final step of the method in accordance with the invention therefore consists in collecting the high molecular weight fractions corresponding to the highly branched glucose polymers.

The high molecular weight products may be collected as such, precipitated with ethanol, purified and dried under vacuum for 24 hours or spray-dried, by any technique known to persons skilled in the art.

As will be exemplified below, the Applicant Company has finally found that to vary the content of branched medium chains (DP of between 15 and 25) of the soluble branched glucose polymers in accordance with the invention, it is necessary to vary the amylose content of the starch.

Indeed, the higher the amylose content of the starch used as starting material, the lower the content of branched chains with a DP of between 15 and 25 of the products obtained.

A starch will be preferably chosen whose amylose content is between at least 30% and at most 40% in order to obtain the first family of polymers in accordance with the invention, having at least 14% to at most 16% with a DP of between 15 and 25. Standard pea starches are particularly suitable for the production of this first family.

A starch will be preferably chosen whose amylose content is between at least 40% and at most 60% in order to obtain the second family of polymers in accordance with the invention, having at least 12% to at most 14% with a DP of between 15 and 25.

A starch will be finally chosen whose amylose content is between at least 60% and at most 80% in order to obtain the second family of polymers in accordance with the invention, having at least 10% to at most 12% with a DP of between 15 and 25.

The particular physicochemical characteristics of the polymers according to the invention make them advantageously destined for food and medical applications and still more particularly as source of high-energy substrates during physical activity and in the fields of peritoneal dialysis, enteral or parenteral nutrition, blood plasma substitutes, regulation of digestion and diet of diabetics.

Other characteristics and advantages of the invention will emerge on reading the nonlimiting examples described below.

EXAMPLE 1

A starch solution at 10% of dry matter content is prepared from a pea starch having a starch richness of greater than 95% and an amylose content of 36.7%.

For that, 100 g of pea starch on a dry basis are resuspended in one liter of water at room temperature and with stirring.

Complete solubilization of the starch is obtained in a cooker at 145° C. for 3 to 4 minutes, followed by cooling to 70° C. The glycogen branching enzyme purified from *Bacillus stearothermophilus* is continuously added in an amount of 1 ml of enzyme solution at 50 000 U/ml per 100 g of substrate on a dry basis.

The enzymatic reaction is carried out for 21 hours at 70° C. and at pH 6.8 and then stopped by heating at 90° C. for 1 h.

Additional treatment with 0.15 ml of β-amylase (BBA SPE ZYME from GENENCOR at 1500 DP°/ml) per 100 g of starch on a dry basis is carried out in the preceding reaction medium brought to the temperature of 60° C. and to pH 4.9 to 5.

The incubation is carried out for 2 hours, and the reaction is stopped by heating for 1 h at 90° C.

The reaction medium is then ultrafiltered on a membrane with a cut-off of 9000 daltons (ES209 membrane from PCI), and the ultrafiltrate is collected and spray-dried.

Table 1 below presents the results of the physicochemical characteristics (level of α-1,6 bonds, Mw and reducing sugar content) of the soluble branched glucose polymer in accordance with the invention thus obtained.

TABLE I

| | |
|---|---|
| Level of α-1,6 bonds (%) | 14 |
| Mw ($10^5$ daltons) | 0.96 |
| Reducing sugar content (%) | 0.14 |

The percentage of reducing sugars is determined according to the method of SOMOGOYI, described by N. NELSON in A photometric adaptation of the SOMOGOYI method for the determination of glucose, 1944, J. Biol. Chem., 153, pp. 375-380.

The branched chain length distribution profile is then determined as indicated above.

Table II below presents the results obtained.

TABLE II

| | |
|---|---|
| DP 2 to DP 15 (%) | 71.7 |
| DP 15 to DP 25 (%) | 15.4 |
| >DP 25 (%) | 12.9 |

The soluble branched glucose polymer obtained has a remarkable branched chain length distribution which results in slightly more than 70% of short chains (DP of less 15) and slightly less than 30% of medium to long chains (DP greater than 15).

The value of the MARK HOUWINK SAKURADA parameter "a", determined by the methodology described above, is 0.1.

The soluble branched glucose polymer in accordance with the invention therefore has a compact structure, which is folded on itself, with nevertheless still chains which are accessible to enzymatic attacks.

EXAMPLE 2

A comparative study is carried out of the branched chain length distribution profiles of the products of the reaction with the branching enzyme and β-amylase on substrates containing variable contents of amylose.

Waxy maize starch (Starch A), standard maize starch (Starch B), and two varieties of starch rich in amylose containing 50 and 70% of starch respectively (Starches D and E) are then treated in the same manner as described in Example 1. Also presented in this table are the results obtained with pea starch (Starch C) obtained in Example 1.

Table III below presents the quantities of branching enzymes (incubation of 18 to 21 hours) and of β-amylase (treatment of 2 hours) used for the treatment of the different varieties of starch.

TABLE III

|  | Starting starches | | | | |
| --- | --- | --- | --- | --- | --- |
|  | A | B | C | D | E |
| Branching enzyme (ml per 100 g) | 1 | 1 | 1 | 1.5 | 2 |
| SPEZYME BBA (%) | 0.05 | 0.1 | 0.15 | 0.13 | 0.1 |

Table IV presents the results obtained in terms of level of α-1,6 branching, molecular weights and reducing sugar contents of the highly branched glucose polymers thus prepared.

The compounds are identified products F, G, H, I and J, obtained from the starches A, B, C, D and E, respectively. The characteristics of the product F are reproduced in Example 1.

TABLE IV

|  | Products of the reaction | | | | |
| --- | --- | --- | --- | --- | --- |
|  | F | G | H | I | J |
| Levels of α-1,6 bonds (%) | 11.2 | 13.3 | 14 | 15.2 | 13.1 |
| Mw ($10^5$ daltons) | 0.84 | 0.77 | 0.96 | 0.96 | 1.31 |
| Reducing sugar content (%) | 0.2 | 0.015 | 0.14 | 0.39 | 0.29 |

The enzymatic treatments on the three substrates rich in amylose (respective amylose contents of 37.5, 50 and 70%) make it possible to manufacture soluble branched glucose polymers having a level of α-1,6 branching in the narrow range of 13 to 15%, for a molecular weight of between 0.9 and $1.5 \times 10^5$ daltons.

The treatment of waxy maize starch and of standard maize starch, which are moreover described in Patent Application EP 1,369,432, leads to branched glucose polymers having a level of α-1,6 bonds in the range from 11 to 13% and a molecular weight value in the range from 0.7 to $0.9 \times 10^5$ daltons.

The use of starches rich in amylose as starting substrate therefore makes it possible, in a remarkable manner, to obtain soluble highly branched glucose polymers having levels of α-1,6 glucoside bonds and molecular weights which are higher than those obtained from substrates which are richer in amylopectin, which in itself is remarkable.

Table V below assembles the different chain length distribution profiles of the different products obtained. The values of the coefficient of intrinsic viscosity "a" according to MARK HOUWINK SAKURADA are also presented therein.

TABLE V

|  | F | G | H | I | J |
| --- | --- | --- | --- | --- | --- |
| DP 2 to DP 15 | 63.8 | 71.9 | 71.7 | 78.3 | 80.4 |
| DP 15 to DP 25 | 21.8 | 16.3 | 15.4 | 12.6 | 11.5 |
| >DP 25 | 14.4 | 11.8 | 12.9 | 9.1 | 8.1 |
| Coefficient of intrinsic viscosity "a" | 0.12 | 0.12 | 0.1 | 0.08 | 0.09 |

It is observed that the soluble highly branched glucose polymers obtained from starches rich in amylose have from 70 to 85% of short chains, from 10 to 16% of medium chains and from 8 to 13% of long chains.

The soluble highly branched glucose polymers obtained from starches rich in amylopectin contain less than 72% of short chains, more than 16% of medium chains and between 11 and 15% of long chains.

It is also observed that the higher the amylose content of the treated starches, the more the soluble highly branched glucose polymers obtained have a component with a low content of medium size chains.

The soluble highly branched glucose polymers in accordance with the invention therefore have especially a medium chain content of less than 16%, and preferably of between 10 and 16% (which is not the case for the soluble highly branched glucose polymers prepared from standard maize starch and waxy starch).

The measurements of the coefficient of intrinsic viscosity "a" according to MARK HOUWINK SAKURADA also reflect the difference in the degree of compactness of the soluble highly branched glucose polymers obtained.

It is observed that only the starches rich in amylose make it possible to obtain soluble highly branched glucose polymers having a coefficient of intrinsic viscosity value of less than or equal to 0.1.

Moreover, it is also observed that it is possible to vary the degree of compactness of the soluble branched glucose polymers in accordance with the invention by varying the amylose content of the starches used as substrates for the enzymatic reactions.

Consequently, the most compact structures are in fact obtained from the starches which are the most rich in amylose.

EXAMPLE 3

To determine the degree of glucose release, aqueous solutions of soluble highly branched glucose polymers in accordance with the invention are prepared, which are brought into contact with an amylase of pancreatic origin and an intestinal amyloglucosidase (intestinal acetone powder).

The hydrolysis is monitored as a function of time by measuring the glucose appearing over time in the reaction medium.

This test makes it possible to evaluate the resistance of the polymers to hydrolysis by the enzymes involved in the digestion of food carbohydrates.

Two polymers in accordance with the invention (the products H and I of Example 2) are tested in comparison with the glucose polymers obtained from standard starch (the product G of Example 2) whose analysis was made in Patent Application EP 1,369,432 by the Applicant Company, in comparison with glycogen.

The operating conditions for the enzymatic digestion are as follows:

0.6 g of the product to be tested is accurately weighed.

150 ml of sodium maleate buffer 0.1 mol/l at pH 7 are added and the medium is stirred until the product dissolves.

The solution obtained is placed on a water bath for 15 minutes, so that the temperature of the solution is 37° C.

1.5 ml of the solution are removed, 0.15 g of pig pancreatin is added and the medium is incubated for 30 min.

The enzymatic reaction is stopped by placing the samples on a bath to dryness at 100° C., for 10 minutes.

0.75 g of pig pancreatin is added and the medium is incubated for 3 h 30 min at 37° C. on a thermostated bath and with stirring.

Samples are regularly collected during the enzymatic hydrolysis.

The glucose in the samples is then assayed in order to calculate the percentage hydrolysis of the product studied.

This assay is carried out with the aid of a colorimetric method on a HITACHI 704 automatic machine (ROCHE). The reagent used is a reagent containing the enzymes glucose oxidase/peroxidase (GOD/PAP). The volume of reagent used is 500 µl, the sample volume is 5 µl and the reaction temperature is 30° C.

The results are presented in Table VI below.

TABLE VI

| Glucose released | Product G | Product H | Product I |
| --- | --- | --- | --- |
| between 30 and 60 minutes (% on a dry basis) | 36.52 | 27.77 | 29.91 |
| between 60 and 120 minutes (% on a dry basis) | 27.59 | 35.27 | 27.57 |

It is observed that between 30 and 60 minutes of reaction, the soluble highly branched glucose polymers in accordance with the invention (products H and I) prepared from standard pea starch and starch containing 50% of amylose, respectively, release their glucose less rapidly than the glucose polymers (product G) prepared from standard maize starch.

However, this phenomenon is reversed between 60 and 120 minutes, the product H releasing more glucose than the product G.

It appears clearly that the two soluble highly branched glucose polymers H and I in accordance with the invention, prepared from starch rich in amylose, may be used both in nutrition for sports people (the product H releasing after two hours of digestion 63% of glucose with a delayed effect), but also in applications where it is necessary to regulate glycaemia (the product I releasing over time a smaller quantity of glucose than the other products).

It is observed that the choice of the amylose content of the starting starch determines the use of the soluble highly branched glucose polymers in accordance with the invention in well-defined fields of application.

The invention claimed is:

1. Soluble highly branched glucose polymers, having a reducing sugar content of less than 1%, a level of α-1,6 glucoside bonds of between 13 and 17% and a molecular weight having a value of between $0.9 \times 10^5$ and $1.5 \times 10^5$ daltons, wherein the soluble highly branched glucose polymers have a branched chain length distribution profile of 70 to 85% of DP of less than 15, of 10 to 14% of DP of between 15 and 25 and of 8 to 13% of DP greater than 25.

2. The polymers according to claim 1, wherein said soluble highly branched glucose polymers have an intrinsic coefficient of viscosity "a" according to the MARK, HOUWINK and SAKURADA equation of less than or equal to 0.1.

3. The polymers according to claim 1, wherein said soluble highly branched glucose polymers have between at least 12% and at most 14% with a DP of between 15 and 25.

4. The polymers according to claim 1, wherein said soluble highly branched glucose polymers have between at least 10% and at most 12% with a DP of between 15 and 25.

5. A method for preparing the soluble highly branched glucose polymers according to claim 1, comprising:
  i) preparing an aqueous starch solution having an amylose content of at least 30% by weight,
  ii) treating the said solution with a branching enzyme and then a β-amylase successively,
  iii) carrying out a fractionation so as to recover the high molecular weight fractions, and
  iv) collecting the highly branched glucose polymers thus obtained.

6. The method according to claim 5, wherein the aqueous starch solution is treated:
  with 40 000 to 150 000 U of branching enzyme per 100 g of starch, at a temperature of between 25 and 80° C. for a period of 7 to 24 hours,
  and then with 0.05 to 0.5% ml of β-amylase per 100 g of starch, at a temperature of 60° C., a pH of 4.9 to 5, for a period of between 1 and 3 hours.

7. The method according to claim 5, wherein the aqueous starch solution has between at least 40% and at most 60% by weight of amylose.

8. The method according to claim 5, wherein the aqueous starch solution has between at least 60% and at most 80% by weight of standard amylose.

9. A composition comprising the soluble highly branched glucose polymers according to claim 1.

10. The polymers according to claim 2, have between at least 12% and at most 14% with a DP of between 15 and 25.

11. The polymers according to claim 2, have between at least 10% and at most 12% with a DP of between 15 and 25.

12. A method for preparing the soluble highly branched glucose polymers according to claim 2, comprising:
  i) preparing an aqueous starch solution having an amylose content of at least 30% by weight,
  ii) treating the said solution with a branching enzyme and then a β-amylase successively,
  iii) carrying out a fractionation so as to recover the high molecular weight fractions, and
  iv) collecting the highly branched glucose polymers thus obtained.

13. A method for preparing the soluble highly branched glucose polymers according to claim 3, comprising:
  i) preparing an aqueous starch solution having an amylose content of at least 30% by weight,
  ii) treating the said solution with a branching enzyme and then a β-amylase successively,
  iii) carrying out a fractionation so as to recover the high molecular weight fractions, and
  iv) collecting the highly branched glucose polymers thus obtained.

14. A method for preparing the soluble highly branched glucose polymers according to claim 4, comprising:
  i) preparing an aqueous starch solution having an amylose content of at least 30% by weight,
  ii) treating the said solution with a branching enzyme and then a β-amylase successively,
  iii) carrying out a fractionation so as to recover the high molecular weight fractions, and
  iv) collecting the highly branched glucose polymers thus obtained.

15. The method according to claim 5, wherein the amylase contents is between 35 and 80° C.

16. The method according to claim 6, wherein the aqueous starch solution is treated for a period of between 18 and 24 hours, and with α-amylase for 2 hours.

17. The method according to claim 12, wherein the amylase contents is between 35 and 80° C.

18. The method according to claim 13, wherein the amylase contents is between 35 and 80° C.

19. The method according to claim 14, wherein the amylase contents is between 35 and 80° C.

20. The composition according to claim 9, wherein said composition is in the form of a food.

21. The composition according to claim 9, wherein said composition is in the form of a medicinal product.

* * * * *